United States Patent [19]
Hale et al.

[11] Patent Number: 6,135,969
[45] Date of Patent: Oct. 24, 2000

[54] VIBRATION SENSOR

[75] Inventors: Alan Hale, Cheney; Matt Miley; Allan Passey, both of Spokane, all of Wash.

[73] Assignee: XN Technologies, Inc., Cheney, Wash.

[21] Appl. No.: 09/277,502

[22] Filed: Mar. 26, 1999

[51] Int. Cl.$^7$ ................................................. A61B 5/11
[52] U.S. Cl. ........................................................ 600/595
[58] Field of Search ........................ 600/511, 500–502, 600/587, 595, 534, 459; 73/649, 652

[56] References Cited

U.S. PATENT DOCUMENTS

| | | |
|---|---|---|
| 4,456,959 | 6/1984 | Hirano et al. . |
| 4,672,976 | 6/1987 | Kroll . |
| 5,140,992 | 8/1992 | Zuckerwar et al. . |
| 5,209,237 | 5/1993 | Rosenthal . |
| 5,524,631 | 6/1996 | Zahorian et al. . |

OTHER PUBLICATIONS

Hewlett Packard, *Cardiotography Service Manual*, page titled "Transducer 15135 A Heart Sound," Feb. 1974.
Hewlett Packard, *Cardiotography Service Manual*, page titled "Transducer 15135 B Heart Sound," Feb. 1974.
Murata Electronics North America, Inc., *Piezoelectric Devices Catalog P–05–B*, 1995.
Morgan Matroc, Inc., "TP–230 Useful Relationships for Circular Bender Bimorphs", publication date unknown.

*Primary Examiner*—William E. Kamm
*Attorney, Agent, or Firm*—Christensen O'Connor Johnson Kindness PLLC

[57] ABSTRACT

A circular layer of piezoelectric material is supported on a larger substrate disc of a thin somewhat flexible material. Flexing of the disc generates an electrical signal. The substrate disc is weighted at its periphery, and the central portion of the disc is supported on a member for transferring motion or vibration that it is desired to detect. In the preferred embodiment the center support is provided by a pair of bosses projecting into the otherwise hollow interior of a two-part casing that encloses the disc-weight assembly. The weights impart a peripheral inertia that makes the composite unit sensitive to minute vibrations.

19 Claims, 5 Drawing Sheets

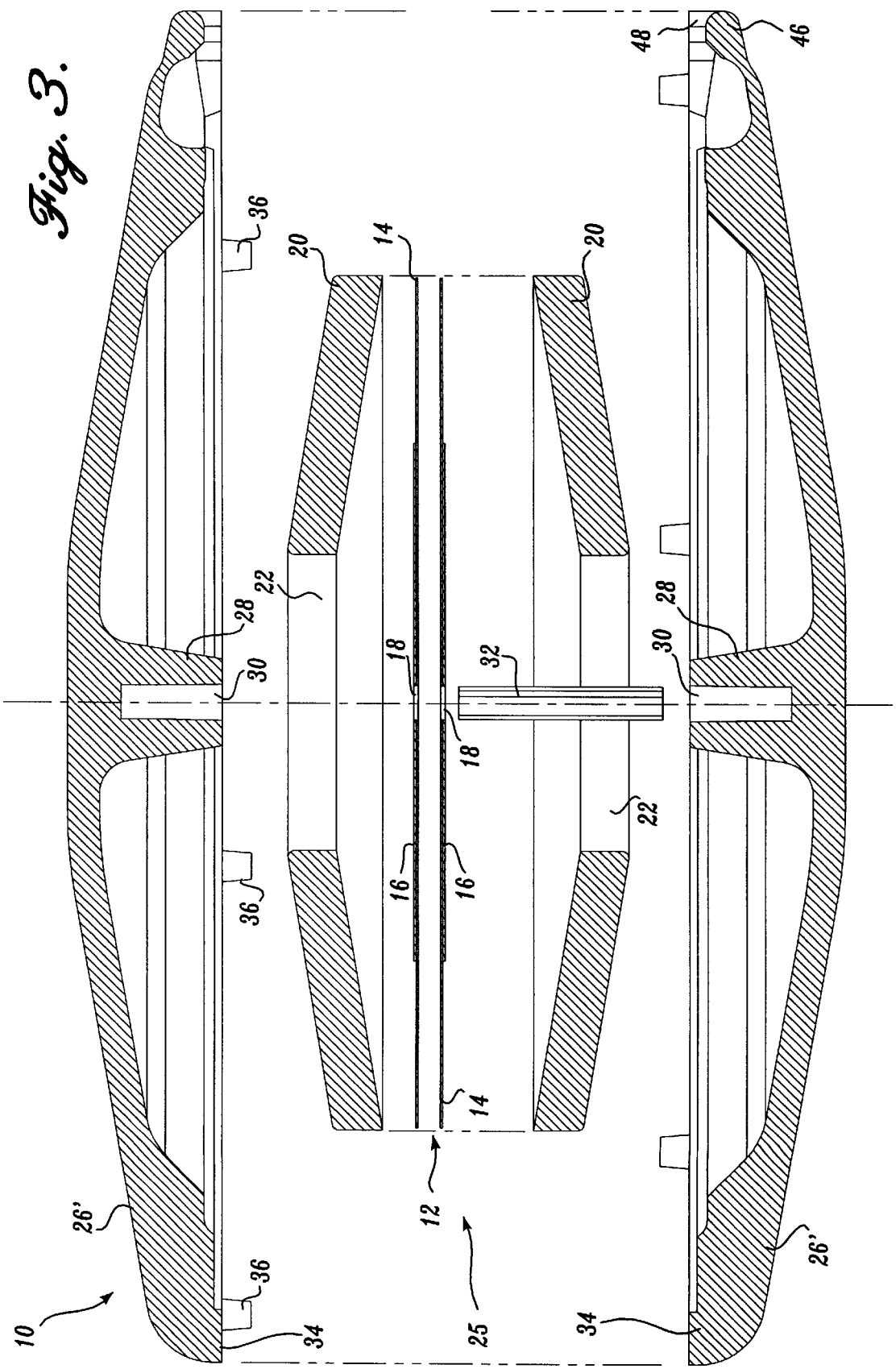

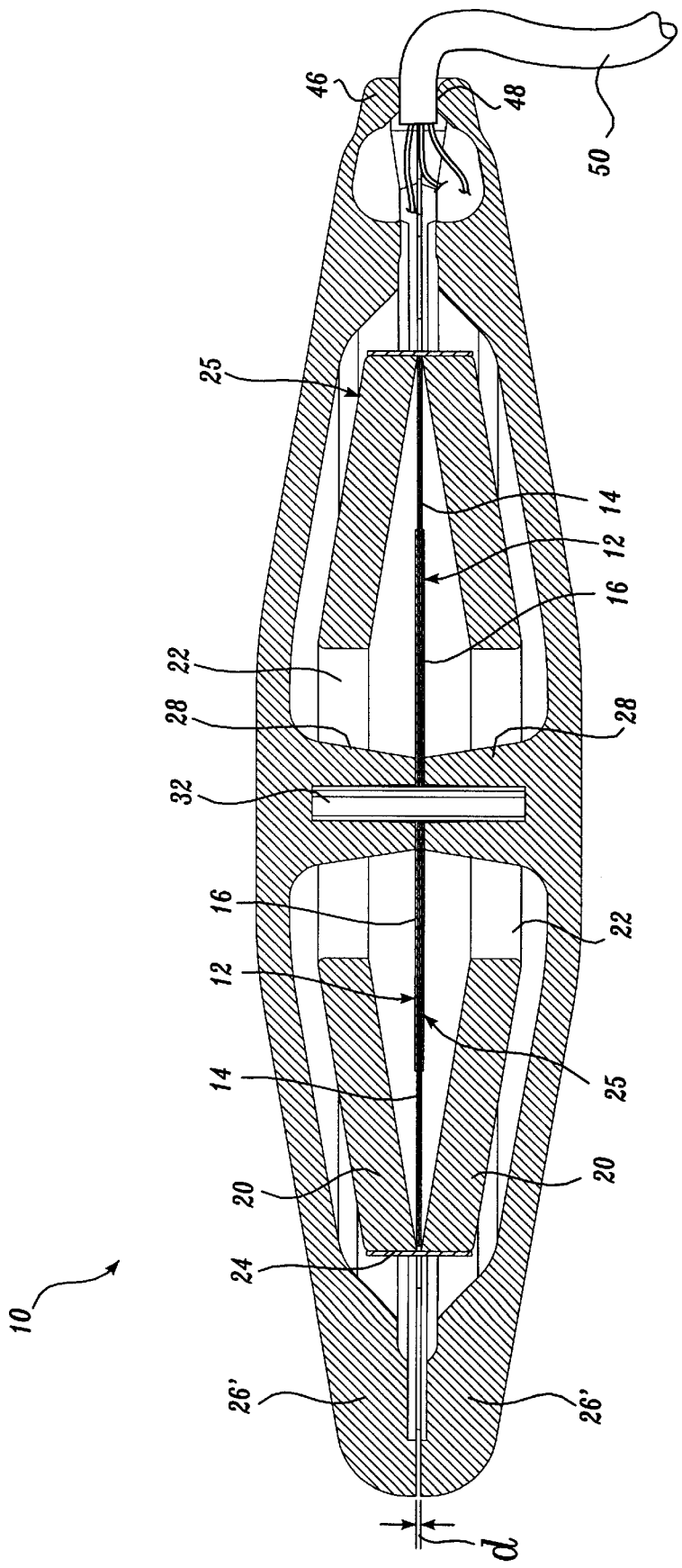

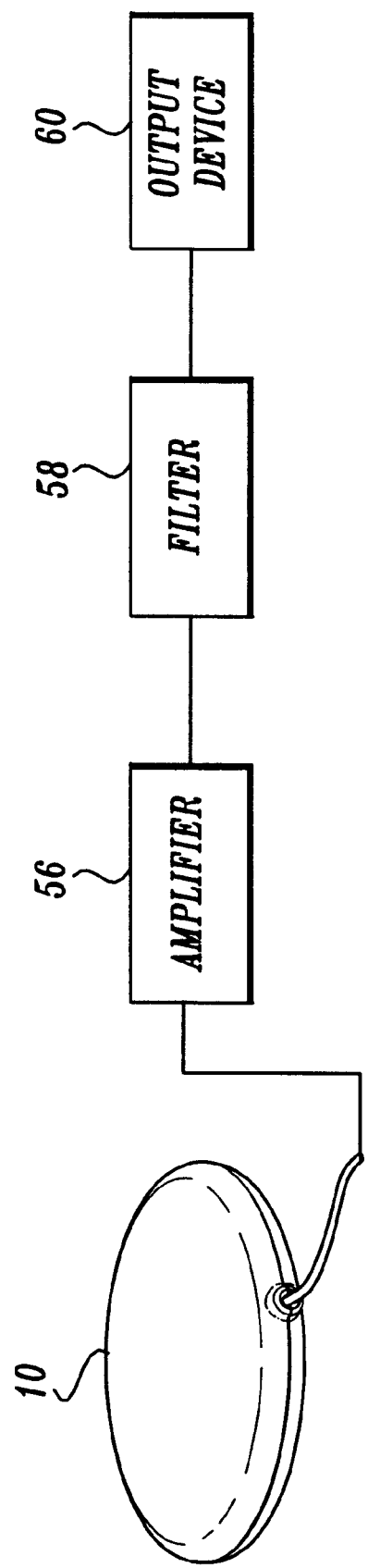

VIBRATION SENSOR

FIELD OF THE INVENTION

The present invention relates to a device for detecting movement having acceleration greater than a predetermined amount, particularly minute vibrations which occur periodically, such as periodic vibrations of maternal skin overlying the abdomen, induced by pounding of a fetal heart in the later stages of pregnancy.

BACKGROUND OF THE INVENTION

One category of motion sensors and fetal heart monitors uses piezoelectric ceramics which typically are mounted on a substrate disc. The substrate, in turn, is supported along its periphery. The supporting element or elements may be mounted in a housing or casing which then is engaged against the matter whose movement or vibration is to be sensed by an actuator member connecting the piezoceramic disc to the vibrating matter. Such movement or vibration induces flexing of the substrate and piezoelectric material, thereby inducing an electrical signal that can be processed to provide an output of the detected motion or vibration.

For example, the "Transducer 15135A Heart Sound" and "Transducer 13135B Heart Sound" devices available from Hewlett-Packard use a piezoelectric crystal transducer mounted on a substrate disc which, in turn, is supported along its peripheral margin. The annular support member for the substrate is carried by a housing that can be engaged tightly against the skin of a patient. Vibration is transmitted to the center of the disc by an actuator which makes contact with the mother's abdomen and the center of the piezo disc. If the magnitude of the vibrations is great enough, vibratory flexing of the substrate and piezoelectric crystal occurs. This results in an electrical signal that can be amplified and processed to detect vibrations within a frequency of interest, namely, vibrations induced by beating of a heart. Consequently, a noninvasive "heart sound" detector is provided.

U.S. Pat. No. 4,672,976 issued on Jun. 16, 1987 to Mark W. Kroll discloses a noninvasive heart sound sensor using an external hydrophone; U.S. Pat. No. 5,140,992 issued Aug. 25, 1992 to Allan J. Zuckerwar discloses a "passive" fetal monitoring system that uses piezoelectric polymer film; and the following patents disclose systems for processing signals from noninvasive heart monitors: U.S. Pat. No. 4,456,959 issued Jun. 26, 1984 to Toshinori Hirano et al., U.S. Pat. No. 5,524,631 issued Jun. 11, 1996 to Stephen A. Zahorian et al., and U.S. Pat. No. 5,209,237 issued May 11, 1993 to Felix Rosenthal.

SUMMARY OF THE INVENTION

The present invention provides a motion/vibration sensor of sturdy, uncomplicated design, and which is adaptable for use in a noninvasive fetal heart sound monitor. In a preferred embodiment, an exterior casing is formed of two identical halves with concave inner surfaces. When the casing halves are brought together they form a hollow interior for a motion/vibration sensing component. Such component includes one or more substrate plates carrying one or more piezoelectric patches. For example, a single substrate plate with a patch on one side can be provided, or identical substrate-patch units mounted back-to-back with the piezoelectric patches exposed. In accordance with the present invention, the piezoelectric unit or units are supported only at their centers by bosses that project into the interior of the casing. These units are clamped between such bosses and can be maintained in alignment by a nonconductive peg extending through their centers and into the bosses. An alternate means of suspension can be obtained by using threaded bosses. A weight or weights are provided at the periphery of the piezoelectric units. In a preferred embodiment, the substrate plates are circular discs and the weights engage the plates at very narrow marginal portions of the discs. This can be achieved by using beveled washers, such as spring washers (Belleville springs), for the weights or other means of achieving peripheral weighting. The spring washers are inclined oppositely from the peripheral edges of the respective substrate discs inward to central apertures or openings of a diameter much greater than the diameters of the center peg and supporting bosses, so as not to interfere with flexing of the piezoelectric units relative to the bosses of the casing. The peripheral inertia added by the weights increases the sensitivity of the sensor to vibrations conveyed through the casing to the centers of the piezoelectric units.

The interior of the casing is shaped to limit the maximum motion permitted by flexing of the piezoelectric unit or units. Such flexing, induced by a vibration applied to the casing or movement having an acceleration greater than a predetermined amount, induces an electric potential (signal) in the piezoelectric material. This signal can be conveyed to the exterior of the casing by a wire, flexible circuit board, or metal boss. Alternatively, the interior of the casing can be coated with a conductive material, and sections of it partitioned to act as conductors for conveying the induced potential to a rim of the casing. Connections to external conductors then need only be made at the rim, rather than having to be attached directly to the piezoelectric patch or patches themselves.

The assembly provides for a very cost-effective and vibration sensitive unit. Signal processing can amplify the induced electrical signals and filter out signals of frequencies other than those of interest. A variety of output devices can be used, including audio (speaker, headphones), visual (display, chart record) or recording or memory components for signal storage and playback.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 3 is a diametral section of the sensor of FIG. 1, with parts shown in exploded relationship;

FIG. 4 is a diametral section corresponding to FIG. 2 but with parts almost completely assembled; and FIG. 5 is a block diagram of a signal processing system and a vibration sensor in accordance with the present invention.

DETAILED DESCRIPTION OF THE PREFERRED EMBODIMENT

Figure 1:
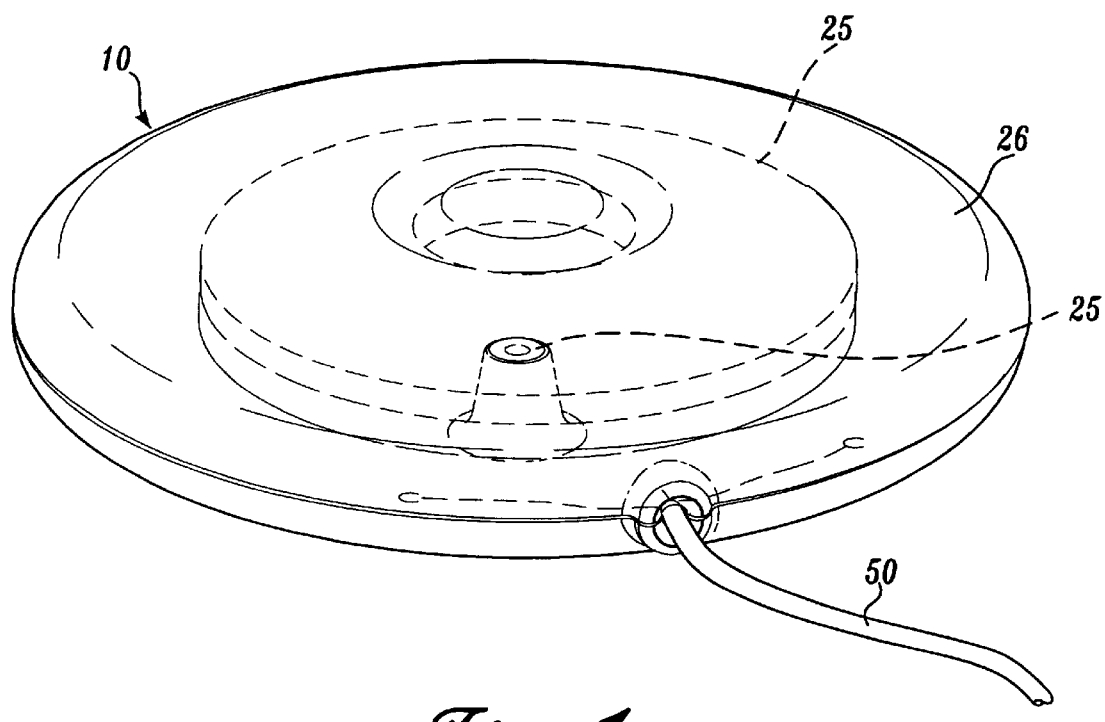
FIG. 1 is a top perspective of a vibration sensor in accordance with the present invention with parts assembled.
Figure 2:
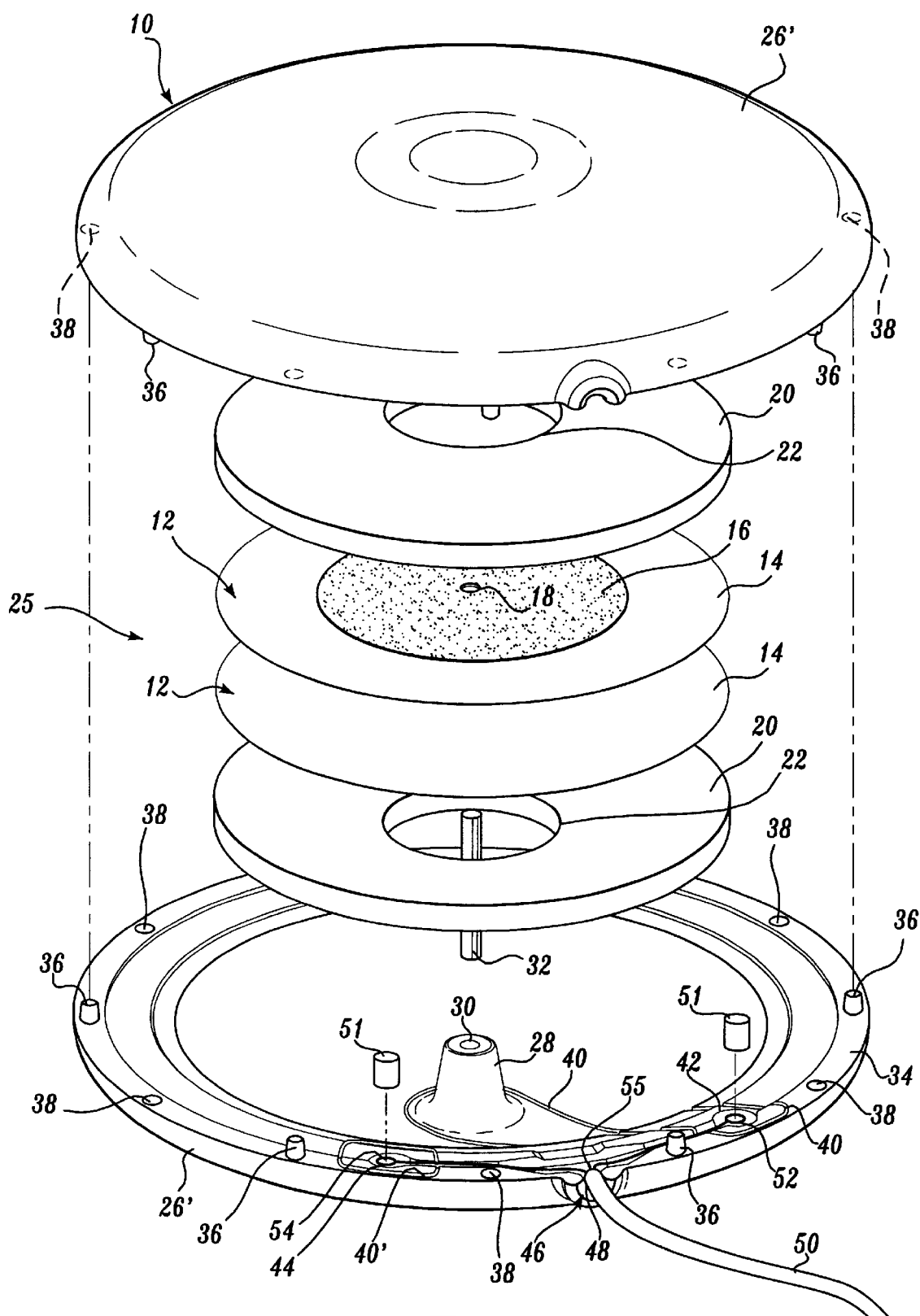
FIG. 2 is a top perspective of a vibration sensor in accordance with the present invention with parts shown in exploded relationship.

With reference to FIGS. 1–4, and particularly FIGS. 2–4 for the internal details, a vibration sensor 10 in accordance with the present invention includes one or more piezoelectric units 12, each of which preferably consists of a thin somewhat flexible substrate 14 and a patch 16 of piezoelectric ceramic deposited on one surface of the substrate. In the illustrated embodiment, each piezoelectric unit is circular, i.e., the substrate 14 is a thin circular disc and the patch 16 is a smaller circular layer of piezoelectric ceramic deposited on the central portion of the disc. In the present invention it is preferred that two such piezoelectric units 12 be used, mounted back-to-back with the piezoelectric patches 16 exposed on the outer substrate surfaces, although this is not considered to be essential in that a single unit 12 could be used. In some cases it is advantageous to use two piezo discs to obtain a true differential signal which may increase the signal to noise ratio in harsh environments. Representative piezoelectric units that can be used are the Model 7NB-41-25DM-1 "external drive piezo-alarm elements" available from Murata Electronics of Smyrna, Ga. These components have a thin (0.10 mm) nickel substrate with an approximately equally thin (0.11 mm) layer or coating of piezoelectric ceramic. In the present invention, however, a small (1.59 mm) hole 18 is punched through the center of each disc, as compared to the discs as manufactured and sold with no through holes.

In accordance with the present invention, the piezoelectric disc or discs 12 are weighted at their peripheries. In the illustrated embodiment, this is accomplished by beveled spring washers (Belleville springs) 20, one at the top and one at the bottom. The outside diameter of each washer is essentially the same as the diameter of the substrate 14 (41 mm in a representative embodiment), such that all weight is applied at a very narrow peripheral margin of the disc or discs, as best seen in FIG. 4. In a representative embodiment, each weight is inclined away from the periphery of the disc 12 that it engages toward a center aperture 22 of a diameter much greater than the diameter of the center holes 18. For example, the diameter of the inner apertures 22 of the weights can be approximately 14.2 mm. The combined weight of the spring washers is several times greater than the weight of the disc or discs. In a representative embodiment, each spring washer can weigh about 22 grams, as compared to the discs which weigh less than 1 gram each.

The assembly of piezoelectric discs 12 and weights 20 (referred to as the sensor component 25) can be completed by a strip 24 of pressure-sensitive adhesive (see FIG. 4) wound around the washers after they are brought together to clamp the discs between them. This method of assembly is preferred but is not considered to be critical. Mechanical fasteners or adhesive could be used, for example.

The composite sensor component 25 is supported in a casing 26 formed of two identical halves 26'. Each half has a center boss 28 projecting axially inward into the otherwise essentially hollow interior of the casing; and each boss has a central blind bore 30 for an alignment peg 32 of nonconductive material such as nylon. Peg 32 is of a diameter only slightly less than the diameter of the central hole 18 through each piezoelectric disc 12, such as 1.57 mm in a representative embodiment. Thus, the sensor component of discs and washers is snugly received on the peg.

The rims 34 of the casing halves have complemental registration pegs 36 and sockets 38 (best seen for the bottom casing half 26' in FIG. 2) for maintaining the halves in a desired relative rotational position when they are brought together. FIG. 4 shows the relationship of the parts with the casing halves in a relaxed condition brought together to where the inner ends of the central bosses 28 have engaged the patches 16 of piezoelectric ceramic adjacent to their center holes. It will be noted that the outer edge portions of the casing halves 26' still are separated slightly (dimension d in FIG. 4), such as by approximately 0.5 mm in a representative embodiment. Thus, when the outer edges are brought firmly together, a clamping force is applied to the center of the piezoelectric discs for maintaining them and the entire sensor component 25 firmly in position due to the stiff resiliency of the casing halves 26'. The casing is formed of a substantially rigid material, such as ABS plastic, and the halves can be secured together by an ABS adhesive. Thus, any vibratory force applied to the exterior of the casing is conveyed by the bosses 28 to the center of the sensor component 25.

Preferably there is a fairly close fit of the weights 20 in the interior of the casing 26. Thus, the degree to which the piezoelectric discs 14 can flex due to vibration or rapid acceleration of the casing 26 is limited. For example, if the magnitude of the vibrations is too great, or an abrupt shock is exerted such as by dropping or rapping the casing on a hard surface, the weights 20 will engage the inner periphery of the casing and prevent or at least deter breakage of the discs or the fragile piezoelectric ceramic. In a representative embodiment a clearance of about 1 mm is provided between the outer surface of each weight and the inner periphery of the adjacent casing half 26'.

The peripheral weighting of the discs 12 achieved by the spring washers 20 (or other peripheral weighting elements) increases inertia in this area and tends to exaggerate disc flexing by motion imparted to the casing. Thus, flexing of the piezoelectric ceramic is increased to produce detectable electric signals. Such signals can be conveyed exteriorly of the casing by wires connected directly to the piezoelectric ceramic. In the illustrated embodiment, however, the interior of each casing half is coated with a conductive material such as Electrodag 550™ by Acheson Colloids Co. of Port Huron, Mich., including the annular section around each center opening of the bores 30 of bosses 28. Thus, with reference to FIG. 2, electric potential induced in a piezoelectric ceramic is conveyed along the conductive coating at the top of the associated boss, along the side of the boss to the interior of the adjacent casing half, and outward toward the casing rim 34. A segregated conductive path can be provided from the boss to the casing rim for attachment of a conductor leading to a signal processing system. In the illustrated embodiment, a continuous race track groove 40 is cut in each casing half, providing an isolated conductive path from the associated piezoelectric ceramic and the boss 28 that it engages, outward toward the rim 34 of the casing to a socket 42 (seen in FIG. 2) for connection of a wire or other conductor. A smaller race track groove 40' is cut around another socket 44 to isolate the mating socket from the remainder of the interior coating. In the illustrated embodiment, two such sockets are provided, one at each side of a nipple 46 having a passage 48 for a three-conductor wire 50. One conductor 52 of the wire connects in one socket 42 to the conductive path from one piezoelectric patch, and the other socket 44 connects a second conductor of 54 of wire 50 to the conductive path from the other piezoelectric patch. The third conductor 55 connects to the remainder of the interior of one or both casing halves to act as a common reference. A small piece of conductive elastomer 51 (10-04-2657-1350 by Chomerics of Woburn, Mass.) may be used in the sockets 42, 44 to secure wires 52, 54 making electrical connection between the mating sockets. The coated interior of the casing could act as an electromagnetic shield to prevent or deter outside signals from contaminating the signals from the piezoelectric patches.

With reference to FIG. 5, the sensor 10 is usable with a signal processor which can include an amplifier 56, filter 58 for passing only frequencies of interest, such as frequencies indicative of fetal heart tones, and an output device 60 which can be an audio output (speakers and/or headphones) or visual output (display and/or chart record) or a memory device for storing the output signal in analog or digital form for future playback.

In accordance with the present invention, the vibration sensor is tuned to have a resonant frequency within the frequency range of interest, which assists in amplifying the vibrations it is desired to detect. This can be accomplished by selection of the size and rigidity of the discs 12 in combination with the amount of peripheral weighting. These factors are easily modifiable to obtain a desired resonant frequency. For use as a fetal heart sound sensor the frequency range of interest can be 20 Hz to 200 Hz and a resonant sensor frequency of 50 Hz to 80 Hz has been found to provide reliable signals of fetal heart tones.

While the preferred embodiment of the invention has been illustrated and described, it will be appreciated that various changes can be made therein without departing from the spirit and scope of the invention. For example, while described with reference to a noninvasive fetal heart sound sensor, which is the application for which the representative embodiment was designed, it is believed that the center mount, peripheral weighted sensor will have other applications as a motion detector, seismic sensor, and other noninvasive medical applications (e.g., breathing and other periodic or nonperiodic motions conveyed from inside the body).

The embodiments of the invention in which an exclusive property or privilege is claimed are defined as follows:

1. A device for detecting motion or vibration comprising a motion/vibration sensor having a first component that generates a signal based on flexing of such first component, the first component having a central portion and a peripheral portion, and a second component supporting the first component at the central portion for transmitting the motion or vibration to be detected to the central portion, the peripheral portion being unsupported so that it is free to move in opposite directions from a rest position by flexing of the first component.

2. The device defined in claim 1, in which the first component is weighted at its periphery to increase peripheral inertia.

3. The device defined in claim 1, in which the second component includes supporting bosses for engaging opposite sides of the central portion, the central portion being clamped between the bosses.

4. The device defined in claim 1, the first component being substantially uniformly weighted around the peripheral margin of the first component.

5. The device defined in claim 1, the second component including a portion adjacent to the peripheral portion of the first component and positioned to limit the maximum amount of motion of the first component peripheral portion.

6. The device defined in claim 5, the maximum limited motion being no greater than an amount which will induce damage to the first component by excessive flexing.

7. The device defined in claim 1, the first component including a substrate disc of a first diameter and a piezoelectric layer supported on the substrate disc and of a diameter smaller than the first diameter, and a peripheral weight engaging the peripheral margin of the substrate disc without engaging the piezoelectric layer.

8. The device defined in claim 7, the mass of the peripheral weight being much greater than the combined mass of the substrate and the piezoelectric layer.

9. The device defined in claim 1, the second component including a casing having a hollow interior with supporting bosses projecting oppositely into the interior, the central portion of the first component being clamped between the bosses.

10. The device defined in claim 9, the interior of the casing being coated with a conductive material.

11. The device defined in claim 10, the interior of the casing having a segregated conductive path for conveying a signal generated by flexing of the first component from one of the supporting bosses toward the outer rim of the casing.

12. The device defined in claim 11, the conductive path being defined by a race track groove formed in the casing, extending through the conductive coating and encompassing the associated supporting boss.

13. The device defined in claim 11, and a weight member engaging the peripheral margin of the first component, the weight member being inclined from the peripheral margin in a direction toward the central portion.

14. The device defined in claim 1, the first component including two piezo discs each having a substrate disc of a first diameter engaged against the other of the substrate discs, the substrate discs each having an exposed piezoelectric layer with such layers disposed oppositely relative to the area of engagement of the substrate discs, and a peripheral weight engaging the peripheral margins of the substrate discs at opposite sides thereof.

15. The device defined in claim 14, the second component including a casing formed in two identical halves, each half having a center supporting boss such that when the casing halves are brought together the bosses engage opposite sides of the assembly of piezo discs.

16. The device defined in claim 15, the casing being constructed and arranged relatively for applying a compressive force against the central portion of the first component when the casing halves are brought together.

17. The device defined in claim 1, the central portion of the first component having a hole therethrough and the second component including an alignment peg extending through the hole.

18. The device defined in claim 1, in which the first component includes a thin disc and a peripheral weight including a beveled washer having a diameter substantially the same as the diameter of the thin disc.

19. The device defined in claim 18, the peripheral weight including two beveled washers disposed, respectively, at opposite sides of the thin disc.

* * * * *